United States Patent [19]

Malik

[11] Patent Number: 6,083,874
[45] Date of Patent: Jul. 4, 2000

[54] COMPOSITION AND METHOD FOR PLANT DESICCATION

[75] Inventor: Nasir S. A. Malik, King of Prussia, Pa.

[73] Assignee: Elf Atochem North America, Inc., Philadelphia, Pa.

[21] Appl. No.: 09/169,064

[22] Filed: Oct. 9, 1998

(Under 37 CFR 1.47)

Related U.S. Application Data

[60] Provisional application No. 60/065,785, Nov. 11, 1997.

[51] Int. Cl.$^7$ .......................... A01N 63/00; A01N 57/00; A01N 43/02
[52] U.S. Cl. .......................... 504/118; 504/128; 504/140; 514/100
[58] Field of Search .............................. 514/100; 504/128, 504/118, 140

[56] References Cited

U.S. PATENT DOCUMENTS

| | | | |
|---|---|---|---|
| 4,226,610 | 10/1980 | Takematsu et al. | 71/86 |
| 5,985,793 | 11/1999 | Sandbrink et al. | 504/116 |
| 6,020,287 | 2/2000 | Brinker et al. | 504/116 |

OTHER PUBLICATIONS

The Agrocchemicals Handbook, 3rd ed., The Royal Society of Chemistry, pp. AO176, AO810, A1014, 1991.

*Primary Examiner*—Jose' G. Dees
*Assistant Examiner*—Alton Pryor
*Attorney, Agent, or Firm*—Gilbert W. Rudman; Stanley A. Marcus

[57] ABSTRACT

This invention relates to an improved composition of matter for and method of desiccating plants such as, for example, cotton. More particularly, this invention relates to an improved desiccating composition comprising a solution of endothall, an ammonium salt, a glutamine synthetase inhibitor, and optionally, a surface active agent, and a method of using the composition.

15 Claims, No Drawings

COMPOSITION AND METHOD FOR PLANT DESICCATION

This application claims the benefit date of provisional application Ser. No. 60/065,785 filed Nov. 11, 1997.

FIELD OF THE INVENTION

This invention relates to synergistically enhancing the desiccant activity of endothall with an ammonium salt, a glutamine synthetase inhibitor and, optionally, a surface active agent.

BACKGROUND OF THE INVENTION

In spite of the international concern about agricultural chemicals, the amount of such chemicals being used continues to grow. Organic chemicals registered have achieved widespread use throughout the world in the production of agronomic and horticultural crops. An agricultural chemical is any substance or mixture of substances that is useful for preventing, destroying, repelling, or mitigating any pest, or is used as a plant growth regulator, seed protectant, defoliant, or desiccant. Examples of agricultural chemicals include herbicides, algicides, plant growth regulators, defoliants and desiccants. While some herbicides may also be desiccant and defoliant agents, the action required for desiccating and defoliating is different from the action required for killing a plant.

There is considerable commercial interest in both desiccants and defoliants as harvest aids used for vegetation management. For example, in intensive cotton cultivation, the use of defoliants is necessary for effective use of plucking machines for harvesting the bolls. For reasons relating to harvesting, defoliation in the form of green leaf parts is preferred to pure desiccation and withering of the remaining plant, since otherwise the fiber quality is very adversely affected by soiling due to withered leaf residues.

Insufficient plant desiccation, however, can be a problem, especially in fields with dense growth, by allowing stem regrowth which complicates harvesting. Sequential applications 7–10 days apart are an option, provided that the grower can afford the additional cost.

The effectiveness of a desiccant is dependent on the quantity applied, the method of application, and the environmental conditions during the application. The objective of the grower or desiccant applicator is to achieve a desired result with the least amount of chemical and at the lowest cost. Therefore, a need exists for an effective and EPA approved desiccant formulation which uses less active ingredients to lessen or avoid adverse environmental effects and to reduce the cost of application.

Sometimes active agricultural chemicals are shown to be more effective in combination than when applied individually. The result is often termed "potentiation" or "synergism" since the combination demonstrates a potency or activity level exceeding that which it would be expected to have, based on a knowledge of the individual potencies of the components.

It is an object of the present invention to provide novel and better desiccants and defoliants and a novel and better method for desiccating and defoliating plants.

SUMMARY OF THE INVENTION

Accordingly, the present invention is directed to a composition for application to chlorophyl-containing plants, the composition comprising (a) endothall, (b) an ammonium salt, (c) a glutamine synthetase inhibitor, and optionally, (d) a surface active agent. It is preferred that the formulation contain a surface active agent.

In the composition the amount of ammonium salt and glutamine synthetase inhibitor are present in an amount effective to increase the desiccant activity of the endothall.

The present invention also provides a method of increasing the effectiveness of the endothall or a salt thereof which comprises applying to chlorophyl-containing plants endothall and an amount of ammonium salt and an glutamine synthetase inhibitor, effective to increase the desiccant activity of the endothall.

The invention thus provides improved performance of endothall or a salt thereof which can result desirably in the use of less endothall, providing both economic and environmental benefits.

Additional advantages of this invention will be set forth in the description which follows, and in part will be apparent from the description, or may be learned by the practice of this invention.

It is to be understood that both the foregoing general description and the following detailed description are exemplary and explanatory only and are not restrictive of the present invention as claimed.

DETAILED DESCRIPTION OF THE INVENTION

Endothall

Endothall, including salts thereof, is a phytotoxicant used to kill chlorophyll-containing vegetation or chlorophyll-containing algae in numerous industrial and non-industrial applications.

Endothall is the common name for the active ingredient (7-oxabicyclo[2,2,1]heptane2,3-dicarboxylic acid) contained in the agricultural products Des-i-cate® and Accelerate®, currently manufactured, formulated, and marketed by Atochem North America (Philadelphia, Pa.).

Accelerate® is registered with the Environmental Protection Agency as a harvest aid for cotton production. As such the product is applied by spraying on cotton plants 1–2 weeks prior to harvest. This kills the leaves and facilitates the mechanical harvesting of the cotton bolls.

Des-i-cate® is registered with the Environmental Protection Agency for use as a potato vine killer and as a harvest aid for alfalfa and clover. In much of the potato acreage throughout the world, the vines are chemically killed ("desiccated") to allow easier passage of the harvesting equipment through the fields. Also, vine desiccation enhances "skin set" on the potato tuber.

Accelerated® and Des-i-cate® products contain mixed mono and di(N,N-dimethylalkylamine) salts of endothall. Accelerate® and Des-i-cate® products contain 5.5 weight percent of endothall. The mono(N,N-dimethylalkylamine) salts are derived from coconut oil.

In a preferred embodiment of the concentrated pesticidal composition, the endothall is the mono (N,N-dimethylalkylamine) salt of endothall. The mono (N,N-dimethylakylamine) salt may be derived from coconut oil.

Endothall is generally marketed as a water soluble formulation. The final formulation of endothall with adjuvant(s) is preferred to be a water-based solution or a stable dispersion in water at the application concentration.

The amount of endothall in the formulation as applied by spray solution is usually in the range of from about 0.1 to about 0.6 percent, preferably 0.12 to 0.25 percent, by weight based on the weight of the total formulation. The amount of endothall applied will range from about 0.1 to 2.0 lbs/acre but preferably will be about 0.25 to 1 lbs/acre, most peerably about 0.5 lbs per acre.

Ammonium Salt

It is known to add ammonium sulfate to endothall composition. However, ammonium has a maximum level at which it can be maintained in a plant and, additionally, ammonium present in the plant is quickly converted to non-toxic metabolites.

The conversion of ammonium to non-toxic nitrogenous metabolites is initiated by glutamine synthetase.

Ammonium salts useful in the present invention include those that while dissolved provide ammonium ion for example, chloride, nitrite, nitrate, sulfate and phosphate.

The amount of ammonium salts in the formulation as applied by spray solution is usually in the range of from about 0.1 to about 6 percent, preferably 0.5 to 2.0 percent, by weight based on the weight of the total formulation.

Glutamine Synthetase Inhibitor

Glutamine synthetase (GS) is a plant enzyme which has a central role in the assimilation of ammonia and in the regulation of nitrogen metabolism. In most plants GS is, via the glutamine synthase/glutamate synthase pathway, the only efficient way to detoxify ammonia. GS catalyzes the formation of glutamine from glutamic acid and ammonia in a reaction driven by the hydrolysis of ATP to ADP and inorganic phosphate. The amide nitrogen of glutamine provides the source of nitrogen for many bisynthetic reactions, including a central role for GS in nitrogen metabolism. The inhibition of GS prevents the biosynthesis of glutamine, thereby preventing ammonia detoxification. Thus, a GS Inhibitor, as used in the present invention, will hinder the metabolism of ammonium to non-toxic metabolites.

The term "glutamine synthetase inhibitor" includes any inhibitor, competitive or noncompetitive, that significantly deceases the glutamine synthetase activity of a plant cell of a given species.

GS inhibitors useful in the present invention include, for example, methionine sulfoxime, tabatoxine-B-lactim, phosphinothricins, such as, glufosinate and bialaphos, oxetin and 5,5-hydroxylsine, as well as other glutamic acid analogues.

The amount of GS inhibitor in the formulation when applied by spray solution preferably is the amount needed to maintain the ammonium ion present in the plant at the maximum level which enhances the effect of endothall. The preferred amount is 50 to 800 ppm, more preferred is about 75 to 500 ppm, most preferred is about 80 to 200 ppm.

Surface Active Agent

Surface active agents preferably are used in the composition and process of the present invention. Surface active agents may affect many properties of the formulation such as solubility, volatility, specific gravity, corrosiveness, efficacy, and freezing and flash points.

Formulations will generally contain one or more surface active agents to promote rapid dispersion of the synergistic components in aqueous medium to form stable, spraying suspensions.

The amount of surface active in a formulation as applied by spray solution is usually in the range of from about 0.1 to about 6 percent, preferably 0.5 to 2.0 percent, by weight based on the weight of the total formulation.

The term "surface active agent" is understood to include surfactants, wetting agents, dispersing agents, emulsifying agents and the like. Such surface active agents, including those suitable for agricultural applications, are well known and reference is made to U.S. Pat. No. , 2,547,724, Columns 3 and 4, for detailed examples of same. Particularly preferred are polyoxyalkylene sorbitan mono-fatty acid salts, such as, polyoxyethylenesorbitan monolaurate marketed under the mark Tween, especially Tween 20 and Tween 80.

Desiccant Composition

A desiccant composition according to the invention may further comprise water or organic solvents. Aqueous compositions, such as solutions or dispersions, are preferred.

The invention also provides a concentrated formulation comprising (a) endothall; (b) ammonium containing salt; (c)glutamine synthetase inhibitor; (d) optionally, a surface active agent; and (d) solvent. It is preferred that the formulation contain a surface active agents.

Most often the concentrated formulations are diluted with water before application. The concentrated pesticidal formulation may itself also contain water, preferably up to about 20 to 50% water.

However, regardless of the dilution the ratio of the components based on the amount of endothall will be as follows: endothall—1 part; ammonium salt—5 to 15 parts; glutamine synthetase inhibitor—0.05–0.5 parts; and surface active agent 0 to 15; preferably 5 to 15 parts.

The solvent may be a substituted or unsubstituted $C_1$–$C_6$ alcohol or substituted or unsubstituted $C_1$–$C_6$ glycol. The solvent may be ethanol, propanol, butylene glycol, propylene glycol, dipropylene glycol, hexylene glycol, glycerine, diethylene glycol, dipropylene glycol monomethyl ether, ethyl acetate, ethyl alcohol, glycerol mono-, di, and triacetate methyl alcohol, sorbitol, butanol, ethylene glycol monobutylether, ethylene glycol monomethylether, isobutyl alcohol, isopropyl alcohol, polyethylene glycol (as defined in 21 C.F.R. 172.260 (a)) n-propanol, N-methyl pyrrolidone, tetrahydrofurfuryl alcohol, and propylene glycol monomethylether. Preferred solvents are propylene glycol and dipropylene glycol.

Additives

Other materials, salts, additives, and/or adjuvants such as oils, surface tension reducing agents, solvents, activators, stabilizers, stickers, foaming or antifoaming agents, emulsifiers, and dispersants known in the art, may be added to the composition or concentrated formulations.

Examples of suitable wetting and dispersing agents are non-ionic aromatic polyethylene glycol ethers, such as Antarox A-400, alkyl aryl polyether alcohol type emulsifiers such as Triton X-100, sulfonated purified lignins such as Reax 45A and Reax45L.

The formulations can contain one or more of any suitable suspending agents, such as for example, methylcellulose, hydroxypropylmethylcellulose, magnesium hydroxide gel, bentonite, Veegum, attapulgite clays, hydroxypropyl guar, aluminum hydroxide gel and the like. The suspending agents will generally be employed in an amount of from about 5 to about 30% by weight based on the weight of the total formulation, and preferably in an amount of from about 15 to 25% by weight. Aluminum hydroxide gel containing about 2 to about 20% by weight, preferably from about 40 to about 10% by weight, aluminum hydroxide is employed as the preferred suspending agent for the formulations of this invention.

Any suitable freeze thaw agent can also be employed in the formulations of this invention, if desired, and is generally present in an amount of from about 1 to about 10% by weight based on the weight based on the weight of the total formulation. Among such suitable freeze thaw agents there can be mentioned, for example, urea, polyhydric alcohols such as glycerol, sorbitol, mannitol, ethylene glycol, propylene glycol, polyethylene glycol, glucose, sucrose and the like as well as water soluble non-toxic polymeric agents such as dextran, polyvinylpyrrolidone and the like. Preferred for use in the formulations of this invention is propylene glycol.

Suitable antifoam agents may also be employed, if desired, and when employed are used in an amount of from about 0.001 to about 0.5% by weight based on the total weight of the formulation. Any suitable antifoam agent can be employed such as, for example a 50% by weight solution of 2,4,7,9-tetrmethyl-5-decyn-4,7-diol known as Surfynol 104-E.

Method of Application

The invention also provides a method of increasing the effectiveness of endothall or a salt thereof which comprises applying to chlorophyl-containing plants endothall and an amount of ammonium salt and an glutamine synthetase inhibitor to increase the desiccant activity of the endothall.

The concentrated formulations may be diluted with water to form stable solutions. These stable solutions may be applied to chlorophyl-containing plants using convention agricultural spray equipment.

The desiccant composition is preferably applied to an exposed portion of the plant. The ammonium salt, glutamine synthetase inhibitor and endothall or a salt thereof may be applied simultaneously or separately and in any order. In a preferred embodiment, the ammonium salt, glutamine synthetase inhibitor, optional, surface active agent, and endothall are applied simultaneously in the form of an aqueous composition which contains all the components.

The plant may be any chlorophyl-containing vegetation and preferably is a commercial or garden crop. For example, the preferred crop may be selected from potato vines, cotton plants, hops, alfalfa, and clover. In a further preferred embodiment, the crop is selected from potato vines and cotton plants.

Application Information

According to this invention, the desiccating activity of endothall is markedly potentiated. Accordingly, application rates from as little as about 0.2 lb/acre to about 1.0 lb/acre, preferably from about 0.4 lb/acre to about 0.6 lb/acre, and most preferably from about 0.45 lb/acre to about 0.55 lb/acre, of endothall can now be utilized in conjunction with an effective desiccant potentiating amount of the ammonium containing salt, about 1 lb/acre to about 5 lb/acre, preferably about 2 lb/acre to about 4 lb/acre, and glutamine synthetase inhibitor, about 0.01 lb/acre to about 0.1 lb/acre, preferably 0.02 lb/acre to about 0.05 lb/acre. Preferably, surface active agent is also present at a concentration of about 1 lb/acre to about 5 lb/acre, preferably about 2 lb/acre to about 4 lb/acre, For spraying purposes, the ingredients are generally dispersed or suspended in a sufficient amount of water or a vegetable oil such as soybean oil, cottonseed oil and the like to give complete and uniform coverage of the cotton foliage and the spray mix can be advantageously applied by air or by ground equipment. Although it is convenient to apply the components simultaneously in one formulation, each can be applied substantially simultaneously in separate formulations with the effect of a combined application.

The compositions according to the invention are obtained in known manner by intimately mixing and/or grinding the three synergistic components with suitable inert carriers, with or without the addition of dispersants, suspending agents or solvents which are inert toward the active components. Pre-mix concentrates such as, for example, wettable powders, slurries and suspendible liquid concentrates In preparing tank mixes, a gallon of such composition may be diluted with from about 2 to about 10 gallons of water for aerial spraying and from about 10 to about 40 gallons of water for ground spraying equipment.

The following examples provide further illustrations demonstrating the enhanced cotton desiccating response obtained from application of the two synergistic components.

EXAMPLES 1 AND 2

Cotton plants were grown in 6" plastic pots filled with PromixBX (Premier Horticultural Inc.) supplemented with modified Hoagland nutrient solution. Plants were grown in a walk-in type growth room maintained at 14 hour photoperiod giving a light intensity of at least 500 $\mu$mole/m$^2$/s at plant height. The temperature in the growth chamber was maintained at ca. 30° C. during day and 28° C. during night, and average relative humidity was kept at ca. 70%. Fully expanded primary leaves, of one month old plants, were treated with 200 $\mu$l of different test solutions. At least four replicate leaves were used for each treatment. After the application of test solution, the plants were placed back in the growth chamber. Plants were scored for various stages of senescence and desiccation one day, two days, and three days after treatment. The effects were visually scored between 0–10. A rating of zero was given when there were no observable effects, and a rating of 10 was given when the leaves were completely dried. The intermediate scores were given based on the extent of senescence/desiccation and the area of the leaf affected.

| RESULTS | | | | | | | | | | | | | |
| --- | --- | --- | --- | --- | --- | --- | --- | --- | --- | --- | --- | --- | --- |
| Formulation | 1 | 2 | A | B | C | D | E | F | G | H | I | J | K |
| Water | √ | √ | √ | √ | √ | √ | √ | √ | √ | √ | √ | √ | √ only |
| Endothall PPM | 300 | 300 | 1000 | 0.0 | 300 | 300 | 0.0 | 0.0 | 300 | 0.0 | 300 | 0.0 | 0.0 |
| $NH_4SO_4$ % | 0.3 | 0.3 | 1 | 0.3 | 0.0 | 0.3 | 0.3 | 0.0 | 0.0 | 0.0 | 0.0 | 0.3 | 0.0 |
| Glufosinate PPM | 150 | 50 | 0 | 150 | 150 | 0.0 | 50 | 150 | 50 | 50 | 0.0 | 0.0 | 0.0 |
| Tween 20 % | 0.1 | 0.1 | 0.1 | 0.1 | 0.1 | 0.1 | 0.1 | 0.1 | 0.1 | 0.1 | 0.1 | 0.1 | 0.0 |
| Score | | | | | | | | | | | | | |
| Day 1 | 8.0 | 6.0 | 8.25 | 3.25 | 3.0 | 2.25 | 1.75 | 0.67 | 0.5 | 0.0 | 0.0 | 0.0 | 0.0 |
| Day 2 | 9.5 | 8.87 | 9.25 | 7.87 | 4.5 | 3.6 | 5 | 2.75 | 1 | 0.0 | .025 | 0.0 | 0.0 |
| Day 3 | 10 | 9.75 | 10.0 | 9.25 | 7.0 | 5.12 | 7.25 | 5.5 | 1.25 | 1.0 | 0.27 | 0.0 | 0.0 |

Discussion of the Results

The mixtures of Example 1 and 2, [endothall (300 ppm), ammonium sulfate (0.3%), glufosinate, (50 ppm and 150 ppm) and 0.1% Tween] gave significantly more powerful desiccation of cotton leaves one day after application than any of the chemicals alone or any combination that excluded either endothall, ammonium sulfate, or glufosinate (except for Comparative A which contained 1000 ppm of endothall instead of Examples 1 and 2's 300 ppm).

The combination of 300 ppm endothall with 150 ppm glufosinate, including 0.3% ammonium sulfate, (Example 1) produced very strong desiccation effect which was equal to the effect of the treatment that included 1000 ppm of endothall and 1% ammonium sulfate but no glufosinate (Comparative A).

Synergism between 300 ppm endothall and 0.3% ammonium sulfate (Example 1) was clear even with a low concentration (50 ppm) of glufosinate (Example 2). Within one day after application of test solutions—Comparative D, Example 1 and Example 2, a more than three time stronger desiccation effect was produced when 150 ppm of glufosinate was included in endothall formulation (300 ppm endothall and 0.3% ammonium sulfate); and a more than two times stronger effect was produced when 50 ppm of glufosinate was used.

It is also clear from the results that the effects of endothall and glufosinate were markedly reduced in the absence of a ammonium sulfate. Ammonium sulfate with surfactant (Comparative J) produced little effect.

Thus, the results clearly show that a combination of endothall, an ammonium salt, and an inhibitor of glutamine synthetase is important for most effective desiccation of leaves. Any of the chemicals from this combination, however, when applied alone (or in combinations where one of the active ingredient (endothall, ammonium sulfate or glufosinate) is missing) does not produce as powerful desiccation effect as their combination.

EXAMPLES 3 TO 5 AND COMPARATIVE EXAMPLE L

A field test was performed on stripper cotton by applying the compositions of the invention and a comparative composition with a field sprayer.

The test area of the field was divided into small plots (1/100th of an acre) and marked with plastic flags.

Test solutions containing different concentrations of glufosinate were prepared before the spray application. The spray nozzles were kept within 6 inches above the plant level to minimize spray drift due to wind. The temperatures at the test site at the time of application and the 7-day period thereafter were approximately between 90–94° F. during early afternoon and between 70–80° F. during the night.

The treated plots were visually scored for the extent of desiccation three days and seven days after the application.

The treated plots were given scores between 0–10 for the extent of desiccation observed. A score of 0 indicated no desiccation while a score of 10 indicate complete desiccation (100%).

Plants sprayed with a solution (Example 3) containing 100 ppm glufosinate (0.033 lbs/acre), 1% of ammonium sulfate (3.3 lbs/acre), 1505 ppm endothall (0.5 lbs/acre) and 1% Tween 20 (3.3 lbs/acre) and diluted with water to achieve a volume consistent with 40 gal/acre application rate showed 83% desiccation after three days and 100% desiccation after 7 days.

Plants sprayed with a solution (Example 4) containing 200 ppm glufosinate (0.033 lbs/acre), 1% of ammonium sulfate (3.3 lbs/acre), 2000 ppm endothall (0.5 lbs/acre) and 1% Tween 20 (3.3 lbs/acre) and diluted with water to achieve a volume consistent with 40 gal/acre application rate showed 83% desiccation after three days and almost complete desiccation (98%, possibly the spray might have drifted a little bit due to the wind) after 7 days.

Plants sprayed with a solution (Example 5) containing 400 ppm glufosinate (0.033 lbs/acre), 1% of ammonium sulfate (3.3 lbs/acre), 1505 ppm endothall (0.5 lbs/acre) and 1% Tween 20 (3.3 lbs/acre) and diluted with water to achieve a volume consistent with 40 gal/acre application rate showed 90% desiccation after three days and 100% desiccation after 7 days.

In adjacent plots that received a composition (Comparative Example L) containing only 1505 ppm endothall (0.5 lbs/acre) and 1.5% ammonium sulfate (5 lbs/acre), only 63% desiccation was observed after 3 days and 70% desiccation after 7 days.

This field test shows that the addition of glufosinate, ammonium sulfate, and Tween 20 to endothall strongly improves the efficacy of endothall as a plant desiccant for cotton crops, so much so that a complete desiccation of the stripper cotton can be achieved.

What is claimed is:

1. A composition for application to chlorophyl-containing algae or plants comprising (a) endothall or a salt thereof, (b) an ammonium salt, (c) a glutamine synthetase inhibitor, and optionally, (d) a surface active agent.

2. The composition of claim 1 wherein the ammonium salt is ammonium chloride, ammonium nitrite, ammonium sulfate or ammonium phosphate.

3. The composition of claim 1 wherein the glutamine synthetase inhibitor is methionine sulfoxine, tabatoxine-B-lactim, phosphinothricins, oxetin or 5,5-hydroxylsine.

4. The composition of claim 1 wherein the glutamine synthetase inhibitor is glufosinate.

5. The composition of claim 1 wherein the surface active agent is a surfactant.

6. The composition of claim 1 in a solution suitable for spray application to the algae or plant comprising (a) 0.1 to 0.6 percent based on the weight of the total formulation, of endothall or a salt thereof, (b) 0.1 to 6 percent based on the weight of the total formulation, of an ammonium salt, (c) 50 to 400 ppm of a glutamine synthetase inhibitor, and (d) 0 to 6 percent based on the weight of the total formulation, of an surface active agent.

7. The composition of claim 1 in formulation wherein for each part of endothall the formulation contains 5 to 15 parts of a ammonium salt, 0.05–0.5 parts of a glutamine synthetase inhibitor, and 0 to 15 parts of a surface active agent.

8. A method of increasing the desiccation effectiveness of endothall or a salt thereof when applied to chlorophyl-containing plants, the method comprising to the plant concurrently therewith an effective amount of (a) an ammonium salt, (b) a glutamine synthetase inhibitor, and optionally, a surface active agent.

9. The method of claim 8 wherein the ammonium salt is ammonium chloride, ammonium nitrite, ammonium sulfate or ammonium phosphate.

10. The method of claim 8 wherein the glutamine synthetase inhibitor is methionine sulfoxine, tabatoxine-B-lactim, phosphinothricins, oxetin or 5,5-hydroxylsine.

11. The method of claim 8 wherein the glutamine synthetase inhibitor is glufosinate.

12. The method of claim 8 wherein the surface active agent is a surfactant.

13. The method of claim 8 wherein the composition is in a solution suitable for spray application to the algae or plant comprising (a) 0.1 to 0.6 percent based on the weight of the total formulation, of endothall or a salt thereof, (b) 0.1 to 6 percent based on the weight of the total formulation, of an ammonium salt, (c) 50 to 400 ppm of a glutamine synthetase inhibitor, and (d) 0 to 6 percent based on the weight of the total formulation, of an surface active agent.

14. The method of claim 8 wherein the composition is a formulation wherein for each part of endothall the formulation contains 5 to 15 parts of a ammonium salt, 0.05–0.5 parts of a glutamine synthetase inhibitor, and 0 to 15 parts of a surface active agent.

15. The method of claim 8 wherein the plant is cotton, potato vine, alfalfa or clover.

* * * * *